United States Patent
Hoang et al.

(10) Patent No.: US 11,723,998 B1
(45) Date of Patent: Aug. 15, 2023

(54) AUTOMATED ROBOTIC SYSTEM AND METHOD FOR SANITIZATION AND DISINFECTION

(71) Applicants: Sherylinn Hoang, Anaheim, CA (US); John Hoang, Anaheim, CA (US)

(72) Inventors: Sherylinn Hoang, Anaheim, CA (US); John Hoang, Anaheim, CA (US)

( * ) Notice: Subject to any disclaimer, the term of this patent is extended or adjusted under 35 U.S.C. 154(b) by 334 days.

(21) Appl. No.: 16/918,253

(22) Filed: Jul. 1, 2020

(51) Int. Cl.
| | |
|---|---|
| *A61L 2/00* | (2006.01) |
| *A61L 2/24* | (2006.01) |
| *A61L 2/10* | (2006.01) |
| *A61L 2/07* | (2006.01) |

(52) U.S. Cl.
CPC .................................. *A61L 2/24* (2013.01); *A61L 2/07* (2013.01); *A61L 2/10* (2013.01); *A61L 2202/11* (2013.01); *A61L 2202/14* (2013.01); *A61L 2202/16* (2013.01); *A61L 2202/17* (2013.01); *A61L 2202/25* (2013.01)

(58) Field of Classification Search
CPC .......... A61L 2/10; A61L 2/24; A61L 2202/25; A61L 2202/16
See application file for complete search history.

(56) References Cited

U.S. PATENT DOCUMENTS

| | | | | |
|---|---|---|---|---|
| 2013/0126760 | A1* | 5/2013 | Klein | A61L 2/10 |
| | | | | 250/492.1 |
| 2015/0320897 | A1* | 11/2015 | Stibich | G02B 5/208 |
| | | | | 250/492.1 |
| 2019/0263680 | A1* | 8/2019 | Dobrinsky | A61L 2/24 |
| 2020/0161069 | A1* | 5/2020 | Ramanand | H01H 83/20 |

FOREIGN PATENT DOCUMENTS

| | | | | |
|---|---|---|---|---|
| DE | 202020001649 U1 | * | 7/2020 | |
| KR | 101742489 B1 | * | 6/2017 | ............... A61L 2/24 |
| WO | WO-2013116566 A1 | * | 8/2013 | ............... A61L 2/10 |

OTHER PUBLICATIONS

KR 101742489 B1 Translation.*
DE-202020001649-U1 Translation.*

* cited by examiner

*Primary Examiner* — Sean E Conley
*Assistant Examiner* — Changru Chen

(57) ABSTRACT

Embodiments disclosed include autonomous robotic systems and methods for disinfecting an environment. An autonomous disinfecting system comprises, in a housing, a first unit comprising a first plurality of UV-C lamps attached to a first wireless base comprising a plurality of wheels. Preferably, the first unit further comprises a docking port for a second unit comprising a second plurality of UV-C lamps attached to a second wireless base, and a motion sensor configured to send a signal to a processing unit comprised in the autonomous disinfecting system wherein the processing unit is configured to shut down the system when it receives a signal indicating a detected movement.

1 Claim, 9 Drawing Sheets

FIG. 4A (FLOOR-BOT)
(TOP VIEW)

FIG. 4B
(BOTTOM VIEW)

FIG. 5A (CHARGING DOCK)

(FRONT VIEW)

FIG 5B
(TOP VIEW)

AUTOMATED ROBOTIC SYSTEM AND METHOD FOR SANITIZATION AND DISINFECTION

BACKGROUND

1. Field of the Invention

This invention relates generally to intelligent, automated robotic systems and methods for cleaning, sanitizing, sterilizing, and disinfecting an environment.

2. Description of the Related Art

Nosocomial infections or Hospital-Acquired Infections are infections that patient's contract in a healthcare setting that were neither present nor developing at the time the patient was admitted. Hospital-Acquired Infections (HAIs) occur in hospitals, long-term care facilities, medical wards, emergency departments, outpatient clinics, physicians' offices, or community health centers. HAIs can be transmitted from one patient to another through direct or indirect contact. While person-to-person touch is an important mode of transmission, contaminated surfaces in a health care setting of facility can contribute to the transmission of microorganisms causing deadly HAIs. Viruses and bacteria can survive on surfaces for long periods and thrive on many objects, such as bed rails, call buttons, telephones, door handles, mattresses, bathroom fixtures, and chairs. For example, some of the most common HAIs such as *C. difficile* spores can survive in the health care environment for up to 5 months, and Methicillin-resistant *Staphylococcus aureus* (MRSA) and Vancomycin Resistant Enterococci (VRE) can survive on dry surfaces for several weeks to months.

According to the Centers for Disease Control (CDC), in American hospitals alone, HAIs accounts for an estimated 1.7 million infections and 99,000 associated deaths each year.

Embodiments of the present invention attempt to significantly reduce those numbers and prevent HAIs, to promote a safe and healthy environment worldwide.

There remains a need for systems and methods that can ensure a clean, sterilized and sanitized environment. There remains a further need, especially in health care centers to ensure that patients once discharged do not find themselves readmitted due to infections picked up from the very health care centers where they were meant to be cured. There also remains a need for a system and method to kill viral and bacterial pathogens via airborne transmission and droplets that causes dangerous and deadly diseases in a public and private setting. Embodiments disclosed address precisely such a need.

SUMMARY

An autonomous disinfecting system comprising a housing, a first unit comprising a first plurality of UV-C lamps attached to a first wireless base comprising a plurality of wheels and comprised in the housing. Preferably, the first unit further comprises a docking port for a second unit comprising a second plurality of UV-C lamps attached to a second wireless base, and a motion sensor configured to send a signal to a processing unit comprised in the autonomous disinfecting system wherein the processing unit is configured to shut down the system when it receives a signal indicating a detected movement.

In an autonomous disinfecting system, a method comprising emitting UV-C light from a first unit comprising a first plurality of UV-C lamps attached to a first wireless base comprising a plurality of wheels and comprised in the housing. According to an embodiment, the method further comprises releasing a second unit from a docking port comprised in the first unit, and emitting from the second unit UV-C light from a second plurality of UV-C lamps attached to a second wireless base. Preferably the method includes shutting down the autonomous disinfecting system based on a motion detected by a 360-degree motion sensor configured to send a signal to a processing unit comprised in the autonomous disinfecting system wherein the processing unit is configured to shut down the system when it receives a signal indicating a detected movement.

DETAILED DESCRIPTION

The following is a detailed description of embodiments of the invention depicted in the accompanying drawings. The embodiments are introduced in such detail as to clearly communicate the invention. However, the embodiment(s) presented herein are merely illustrative, and are not intended to limit the anticipated variations of such embodiments; on the contrary, the intention is to cover all modifications, equivalents, and alternatives falling within the spirit and scope of the appended claims. The detailed descriptions below are designed to make such embodiments obvious to those of ordinary skill in the art.

Embodiments disclosed are configured to ensure a clean, sterilized and sanitized environment. Embodiments disclosed endeavor create an environment, wherein patients discharge from a hospital or health care facility healthier, not to find themselves readmitted for a new illness due to a contaminated room. An embodiment includes an autonomous, intelligent robot comprising a two in one unit. A main unit holds multiple UV-C lamps and sits on a wireless base with wheels to allow a convenient and easy way to maneuver throughout its surrounding. Within the base is housed a second unit. The second unit comprises a smart low-profile, wireless floor-bot designed to automatically navigate a room and disinfect underneath hospital beds, surgical tables, over-bed tables, and furniture where the UV-C light from the main unit can't reach.

The main unit is an intelligent robot that not only kills disease causing pathogens, but also improves air quality and reduces manual labor with the use of the UV-C lamps. According to an embodiment illustrated in FIG. 1, the autonomous robot comprises a 360-degree motion sensor 102 located in the center and at the very top of the unit to automatically shut off while UV-C light is being emitted once it recognizes a motion as UV-C light affects the human skin and eyes. Standing vertically below the motion sensor are multiple UV-C lamps 104 with multiple corresponding reflectors 105 constructed of polytetrafluoroethylene (PTFE) which initially shield the lamps when turned off to prevent damage to the lamps during transportation of the unit. According to an embodiment, once the unit is powered on, the PTFE reflectors 105 are rotatable and configured to automatically rotate to position themselves behind each lamp. PTFE reflectors 105 are used due to their lighting efficacy of over 97% average reflectance and its ability to evenly distribute the UV-C light in all directions allowing the light to spread across surfaces and eliminate cold spots where pathogens may survive. Preferably, an embodiment comprises a radiometer to monitor individual UV-C output. This is particularly important because once the quality of the lamp is degraded, it will lose its effectiveness and minimize the level of disinfection which in result, will leave areas to remain contaminated.

An embodiment includes a pathogen detector enabling the autonomous robot to automatically detect infectious contaminants in the air and on surfaces. Preferably, a microbial detection sensor continuously monitors pathogens within the area and via a wireless network remotely sends notifications to a mobile phone, PC or tablet when contamination is detected. The microbial detection sensor enables the autonomous robot to determine the length of time required to emit the UV-C light to effectively kill the detected pathogen(s). An early detection of dangerous pathogens is key to help prevent an outbreak from occurring. Embodiments disclosed are configured to detect, alert, and destroy highly contagious pathogens to provide a safer and healthier environment.

According to an embodiment, the autonomous robot comprises a smart sensor configured to enable the autonomous robot to automatically calculate the appropriate UV-C dosage required to disinfect the area based on the room size, shape, and color as these are all important factors to the disinfecting time. If the disinfecting time does not meet the required time for a thorough disinfection, it will result in contaminated areas causing deadly and highly contagious pathogens to live in the air and on surfaces which are easily transmitted. Embodiments disclosed are designed to create a germ-free environment, drastically reducing the transmission of airborne and direct contact diseases.

An embodiment includes a Visual Simultaneous Localization and Mapping (VSLAM) module, enabling the autonomous robot to independently navigate its' surrounding area. According to an embodiment the autonomous robot can navigate itself from its charging station to a specified room or location with just a touch of a few buttons from a mobile phone, PC or tablet via a wireless network. An alternate embodiment enables the autonomous to self-navigate based on pre-configured settings and historic activity. An embodiment includes a software driven application that enables the robot to notify the user once it reaches its destination, the process of the disinfection, completion of disinfection, etc. Preferably, the software driven application enables a manual or automatic safety check wherein a list of several safety questions that must be checked off by the user manually (or automatically by the robot) before it will automatically power on. It takes several minutes for the lamps to warm up before they are fully effective. Once the lamps complete the warmup, the each lamp emits UV-C light of a configurable wavelength and begins sanitizing its' surrounding. According to one embodiment, it takes approximately 5 minutes to fully disinfect an average size bathroom of 50 square feet, approximately 10 minutes to disinfect a hospital room with an average area of 350 square feet, and approximately 25-30 minutes to disinfect an area of 1,000 square feet. An embodiment comprises an additional sensor specifically configured to identify the size of the room it is disinfecting and to automatically determine the length of time required for emitting the UV-C light. During the process of disinfection, the robot will move throughout the room making multiple stops to emit UV-C light in shadowed areas to ensure a maximum coverage of disinfection.

Figure 1:
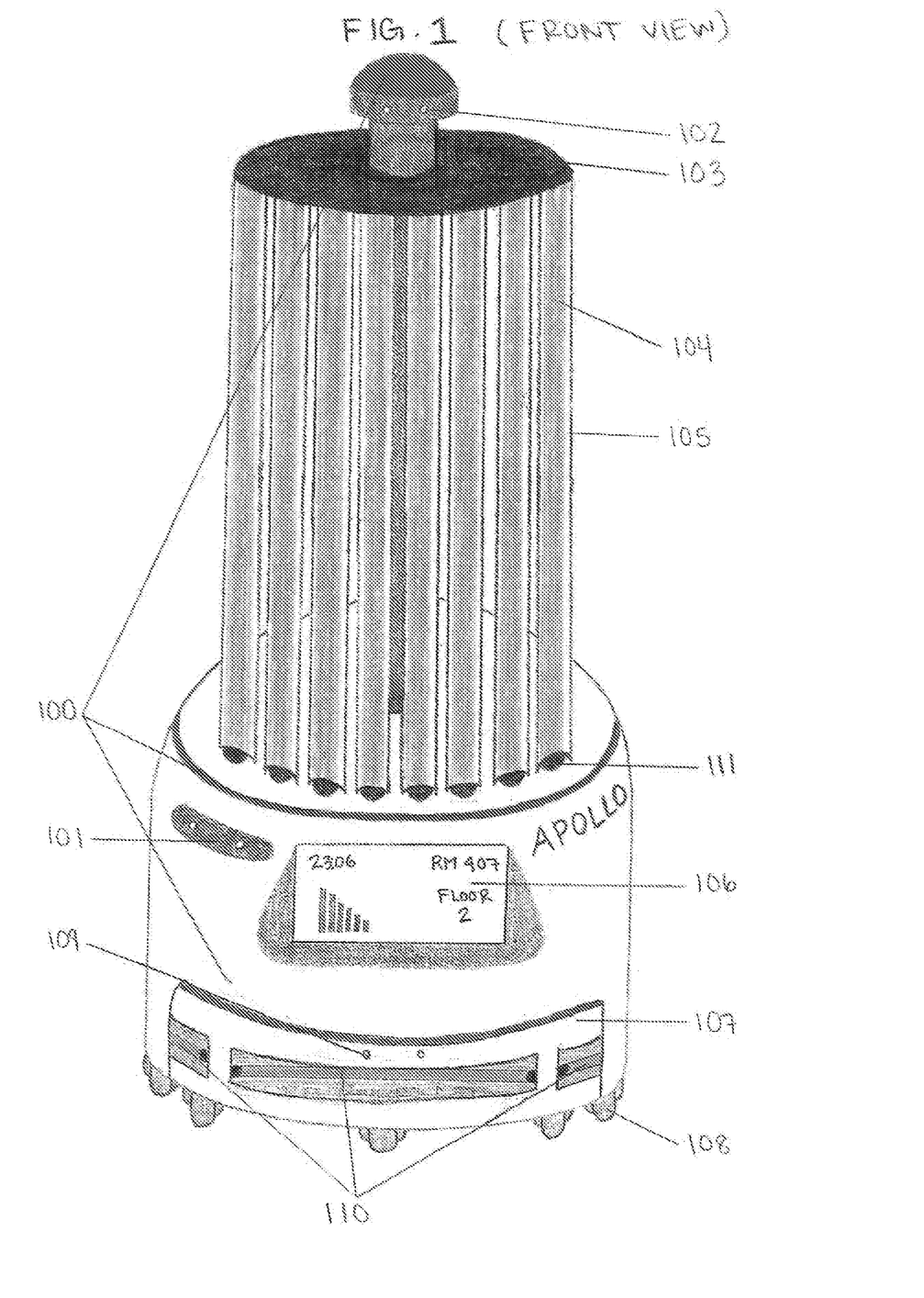
FIG. 1 illustrates the front view of a preferred embodiment of the invention.

FIG. 1 illustrates the front view of a preferred embodiment of the invention. The depicted embodiment illustrates LED lights 100, a simultaneous localization mapping (SLAM) sensor 101, top mounted motion sensors 102, a cap/covering 103 to securely fasten UV-C lamps 104 and PTFE reflectors 105. Further, FIG. 1 depicts an angular LCD display 106 and the auto detachable UV-C floor bot 107. The depicted embodiment includes a plurality of 360-degree swivel heavy duty wheels 108 and a visual simultaneous localization mapping (VSLAM) sensor 109 comprised in the floor bot. The floor bot comprises additional UV-C lamps 110 and the unit includes a socket 111.

Figure 2:
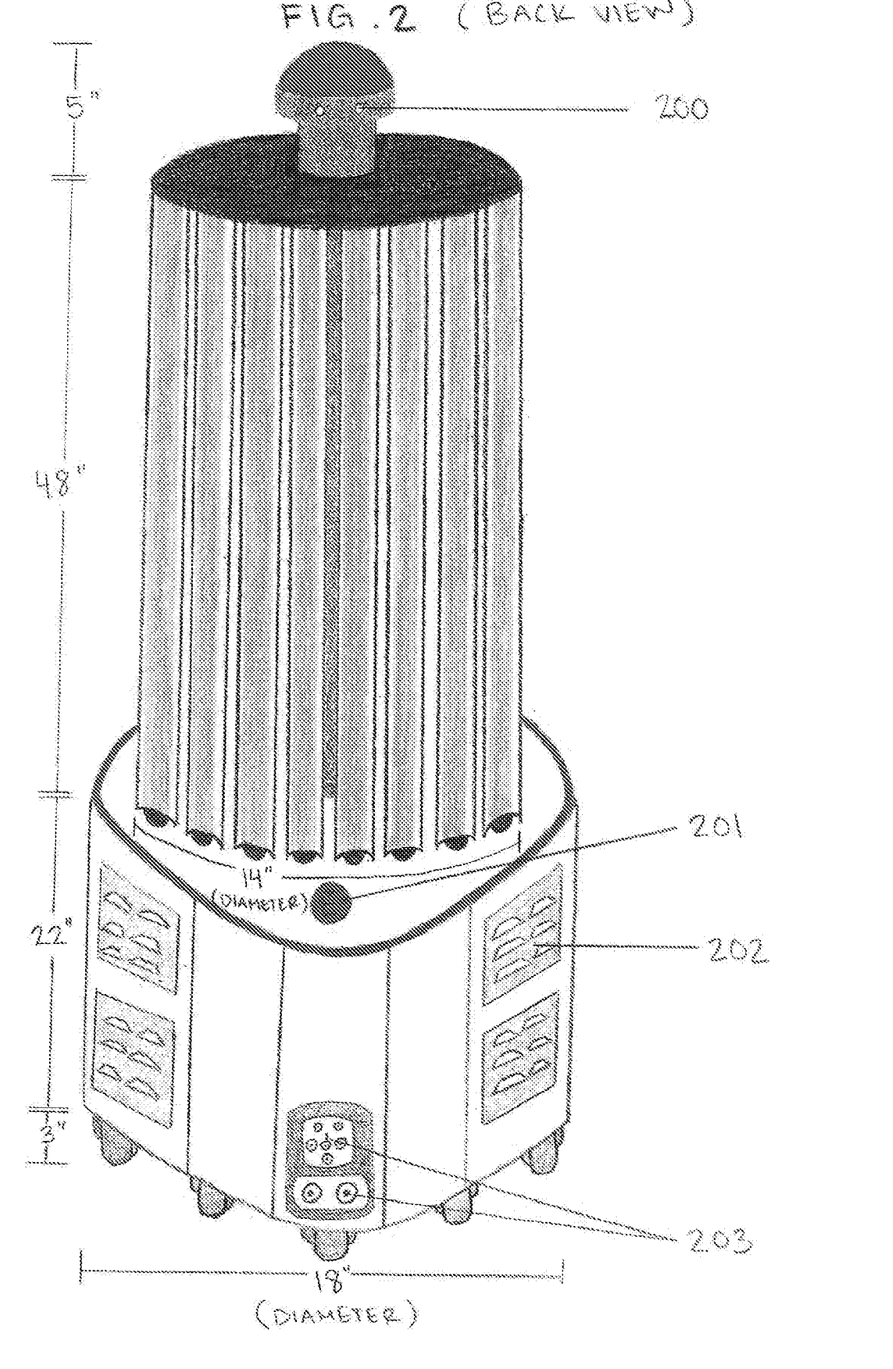
FIG. 2 illustrates the rear view of the preferred embodiment of the invention.

FIG. 2 illustrates the rear view of the preferred embodiment of the invention. The depicted embodiment illustrates the 360-degree motion sensor 200, an emergency stop button 201, air vents 202, and a type 2 CCS+ AC plug socket 203.

Figure 3:
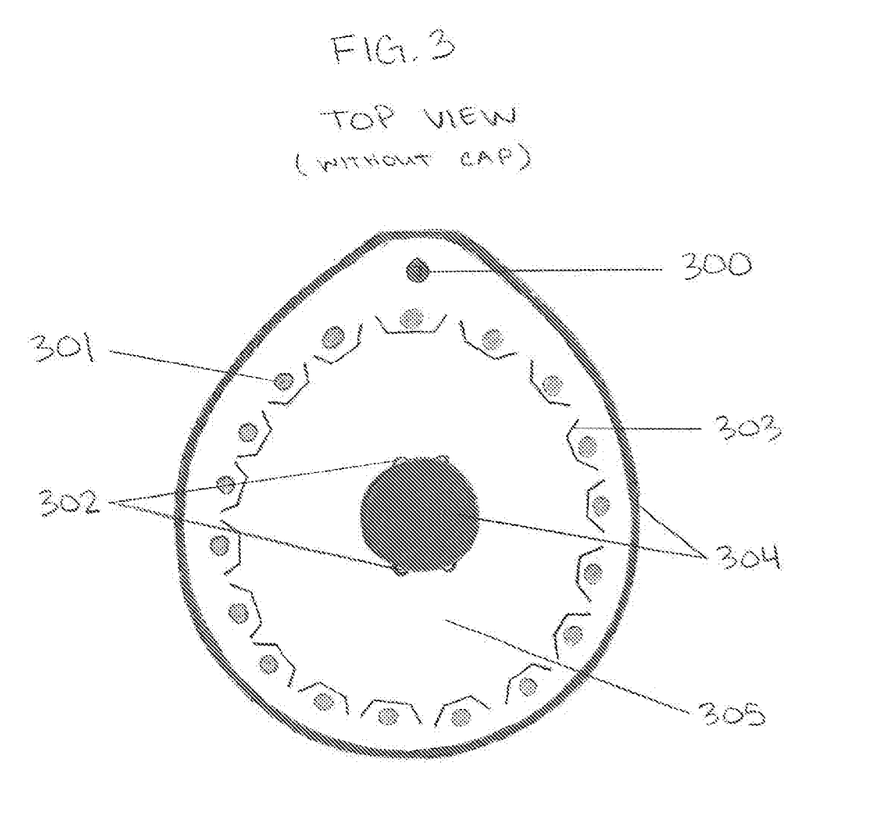
FIG. 3 illustrates the top view of the preferred embodiment of the invention.

FIG. 3 illustrates the top view of the preferred embodiment of the invention depicting the emergency stop button 300, UV-C lamps 301, 360-degree motion sensor 302, PTFE reflectors 303, LED light 304, and base 305.

Figure 4A:
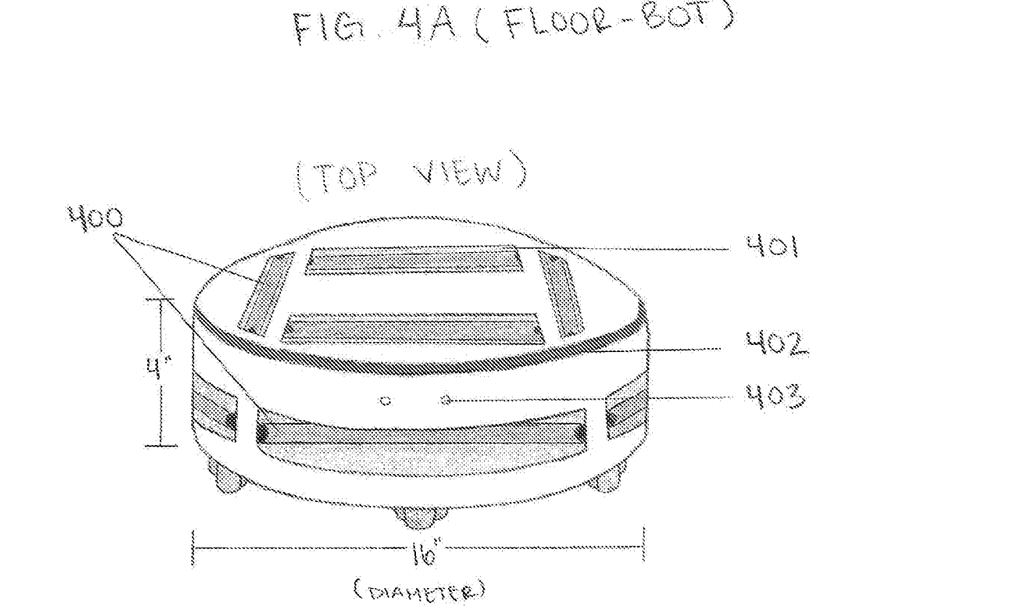
FIGS. 4A and 4B illustrate the top view and bottom view respectively of the UV-C floor bot.
Figure 4B:
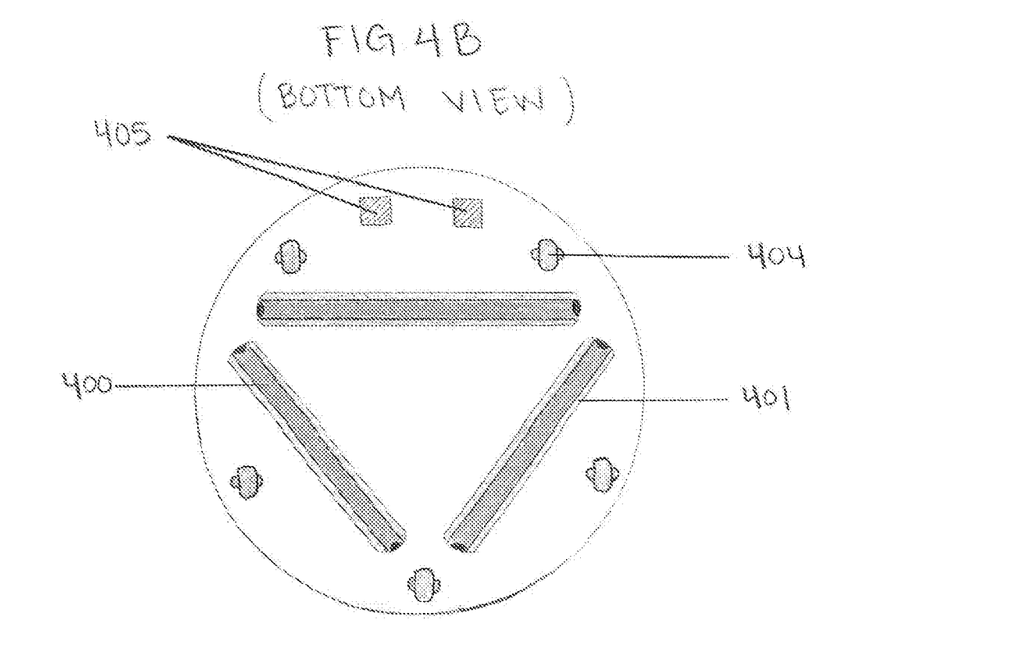

FIGS. 4A and 4B illustrate the top view and bottom view respectively of the UV-C floor bot. The top view of FIG. 4A depicts UV-C lamps 400, PTFE reflectors 401, LED lights 402, VSLAM sensor 403, 360-degree swivel wheels 404 and metal plate 405 for assisting in charging and re-charging the floor bot.

Figure 5A:
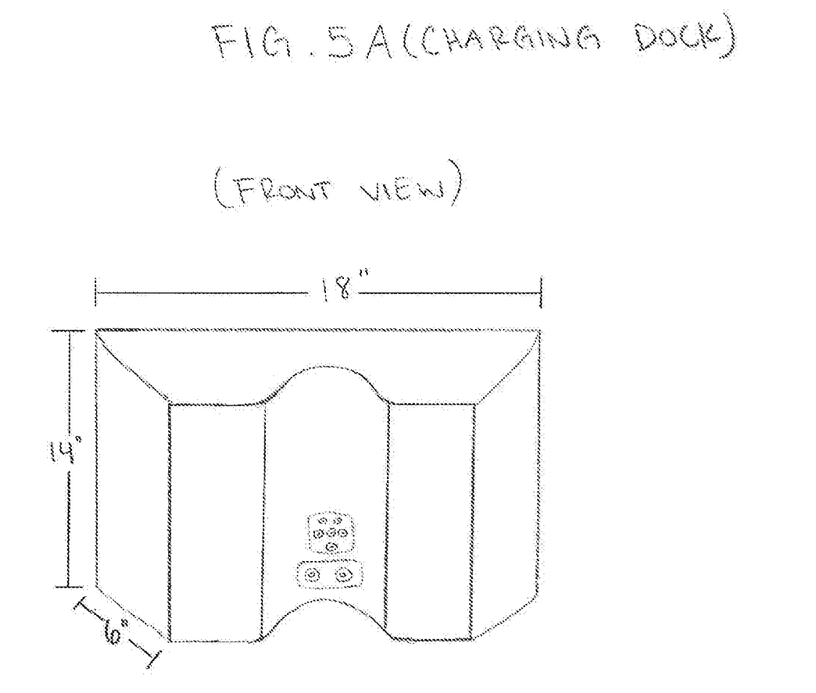
FIGS. 5A and 5B illustrate the front view and top view respectively of the charging dock according to an embodiment.
Figure 5B:
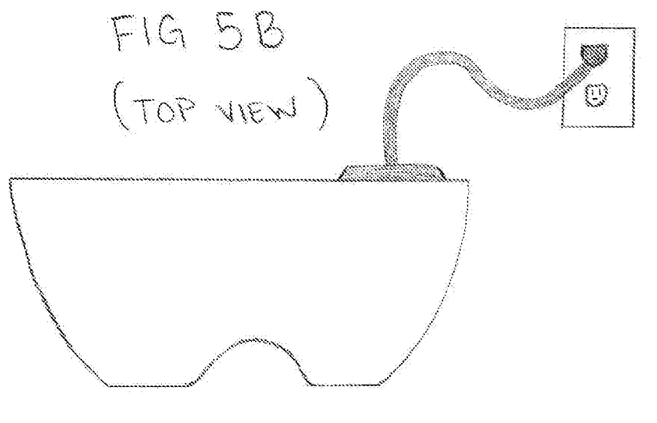

FIGS. 5A and 5B illustrate the front view and top view respectively of the charging dock according to an embodiment. The charging station is stationed and houses a Type 2 CCS plug and socket. It allows the main unit to back-up into the front of the charging station to connect with the Type 2 CCS+ AC plug that is located at the rear of the main unit. The battery life is indicated on the LCD screen that is located on the front of the main base. The LCD screen will also display the time, date, room number it is disinfecting, etc. According to an alternate embodiment, the main unit is battery less and comprises a swiveled extendable wire tether or extension cord that enables the main unit to anchor to the socket and yet move around the room when required.

Figure 6:
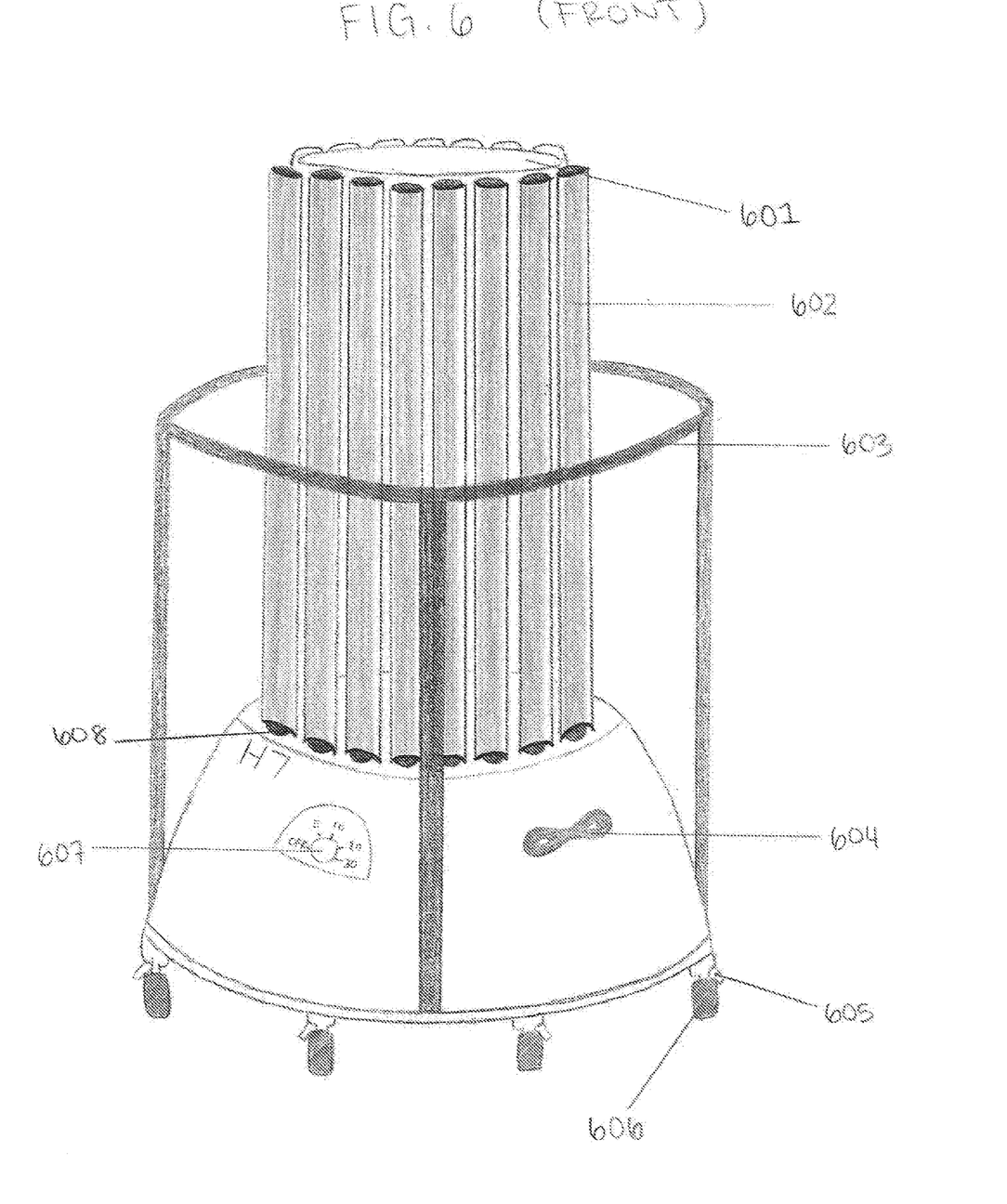
FIG. 6 illustrates a front view of a basic version in one embodiment.

FIG. 6 illustrates a front view of a basic version in one embodiment. The illustrated embodiment depicts aluminum reflectors 601, UV-C lamps 602, a safety handle 603, motion sensor 604, wheel lock 605, wheels 606 and a timing knob 607.

Figure 7:
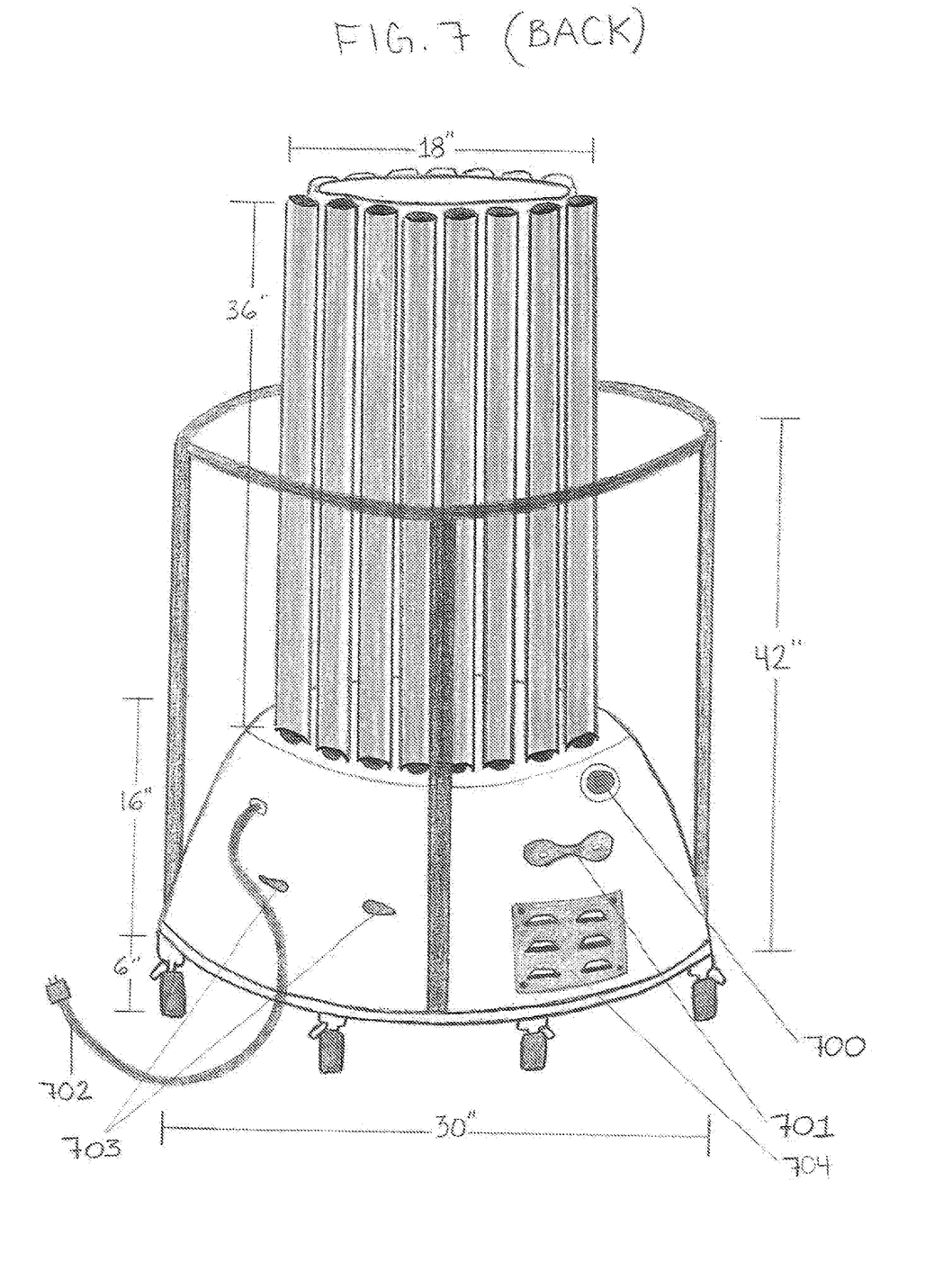
FIG. 7 illustrates a backside view of the basic version in one embodiment.

FIG. 7 illustrates a backside view of the basic version in one embodiment. The illustrated embodiment depicts the dimension of the UV-C lamps, and further depicts emergency shut off button 700, a second motion sensor 701, an electrical cord 702, cord holder 703, and vent for cooling fans 704.

Figure 8:
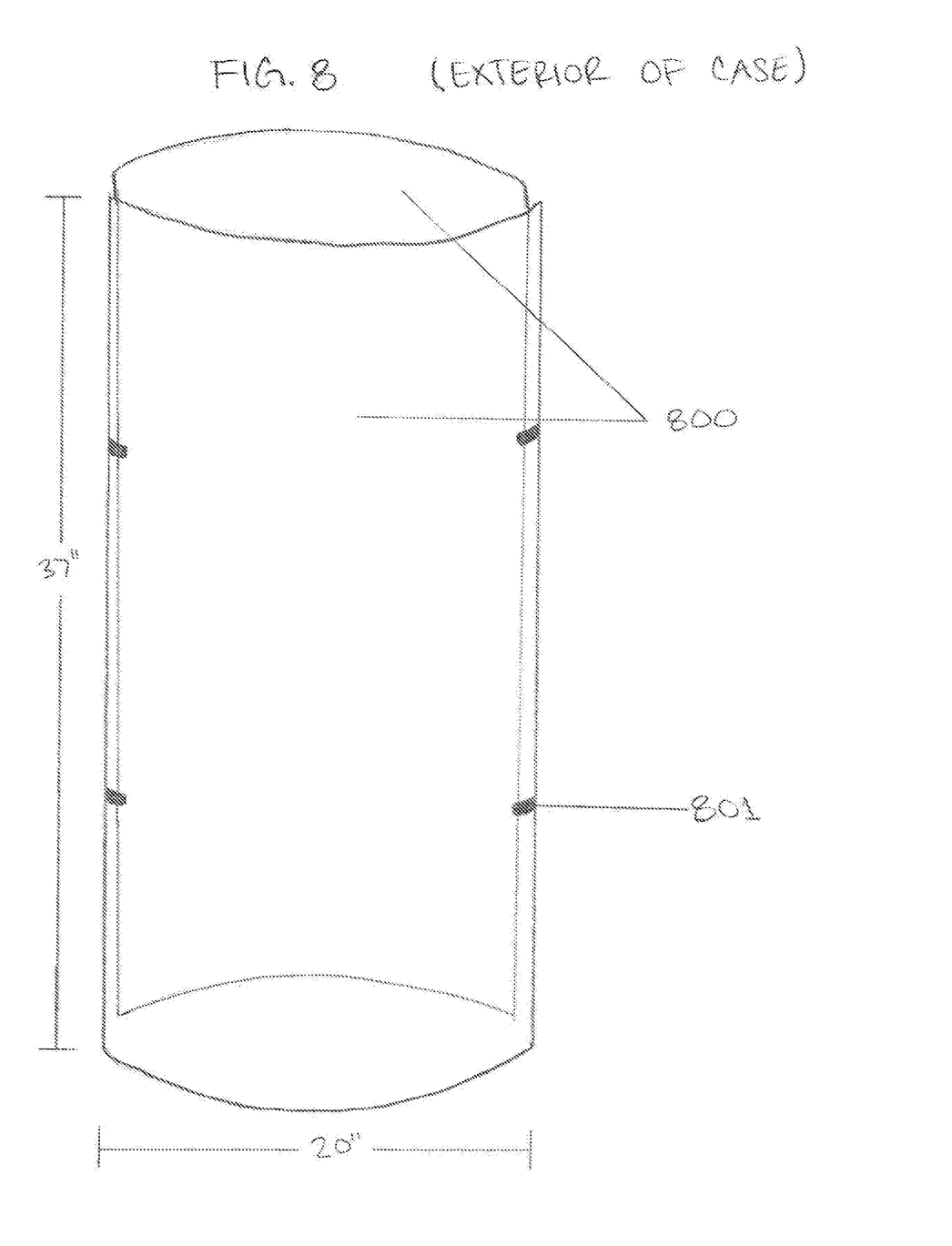
FIG. 8 illustrates a casing for the exterior of an embodiment.

FIG. 8 illustrates an exterior casing of the basic version in one embodiment. The illustrated embodiment depicts plastic casing 800 and four draw bolt latches 801.

Figure 9:
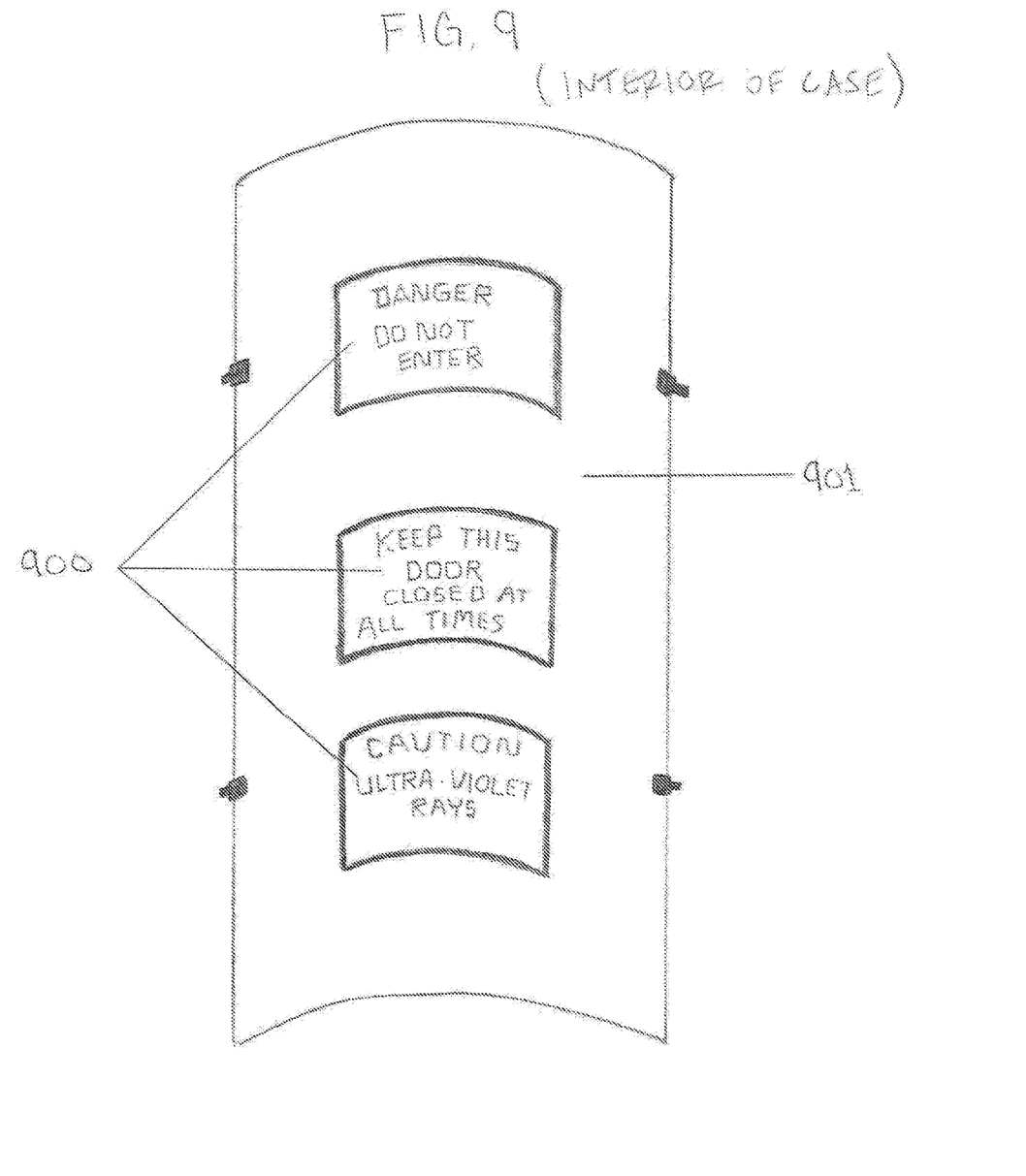
FIG. 9 illustrates an interior of the casing for an embodiment.

FIG. 9 illustrates an interior casing of the basic version in one embodiment. The illustrated embodiment depicts three warning stickers. The casings are to be placed in front of the door of the room being disinfected with the warning stickers exposed to ensure no one enters as the UV-C light is currently in use. Once the disinfection has completed its run time and the UV-C lights automatically turn off, the warning signs can then be removed for safe entry. In one embodiment the autonomous robot is configured to place the warning stickers and pick up the said stickers after its' task is complete.

According to an embodiment, the wireless low-profile floor bot that is housed inside the base can automatically lower its wheels and detach itself to simultaneously begin navigating throughout the floor of the room to disinfect areas that are most likely missed by the main unit, while the main unit is at work. The areas that will require the floor bot to disinfect are underneath hospital beds, surgical tables, overhead tables, and furniture. According to an embodiment, the smart floor bot can emit UV-C light from above to disinfect underneath furniture and fixtures, and from all around its sides as well as underneath to ensure maximum sanitation of the room. According to an alternate embodiment, the floor bot comprises a steam dispenser to steam clean the floor and a rotating microfiber cloth to dry the moisture that remains. Once the floor bot has traveled approximately 150 square feet, the microfiber cloth will automatically rotate. The dirty side of the cloth will automatically rotate to position inside the bot. As the microfiber cloth is rotating, the dry and clean part of the cloth that was located inside the bot will be simultaneously rotated to expose the clean side of the cloth to continue drying the floor. A sensor will send a notification to the mobile phone, PC or tablet of a fully soiled microfiber cloth to replace it. According to an embodiment, the floor bot is controlled by a processing unit coupled to a memory element comprising encoded instructions. The memory element is also configured to remember the historical navigation of the floor bot so it doesn't repeat unnecessary disinfection time. Once it has completed its job, the floor bot returns to the main unit and dock to charge within the base of the main unit. When both of the units have fully disinfected the room, the autonomous robot notifies the user of its completion via notification on a user mobile phone, PC or tablet and begins the next task in que. The autonomous robot can continue to disinfect a different room or automatically navigate to dock to its charging station. Preferably, the autonomous robot can be configured to disinfect an entire service area, i.e. a single room, multiple rooms, an entire floor etc. without manual intervention.

This unique 2 in 1 robot can operate via WIFI with an app or wireless remote controlling device. The app or/and wireless remote controlling device can not only have multiple functions, but it can also have a record of tasks completed, areas disinfected, and identities of user's accessing and operating the unit.

According to an embodiment of the Automated Robot, the robot weighs approximately 100-150 pounds at the heaviest. With newly integrated technologies available today, our goal is to minimize the size and weight of the unit as a whole for convenience and accessibility.

What is UV-C?

There are three types of UV rays: UV-A (315-399 nm), UV-B (280 to 314 nm), and UV-C (100-279 nm). UV-C light is a short-wavelength, ultraviolet light that kills or inactivates microorganisms such as viruses, bacteria, molds, and other pathogens by destroying nucleic acids and disrupting their DNA, leaving them unable to perform vital cellular functions. UV-C light is germicidal and lethal to all forms of microorganisms without the use of high temperature and pressure, chemicals or gases. UV irradiation is an effective, environmentally-friendly and chemical-free way to prevent microorganisms from replicating in any environment.

Embodiments disclosed distinguish the present invention from prior art substantially and significantly. An embodiment includes Polytetrafluoroethylene (PTFE) Reflectors: The use of reflectors increases the effectiveness and UV intensity. Reflectors maximizes internal reflection to take full advantage of the UV energy or photons emitted from the light source. PTFE is one of the few known materials that have radiation profile shaping elements that can improve performance and reflectivity. It can also be an economical way of intensifying the Ultraviolet Germicidal Irradiation (UVGI). Porous PTFE is an excellent material choice for UV reflectivity because of its resistance to degradation, high reflectivity, and diffuse (Lambertian) reflectance. It converts a narrow, directional light source into a wider illuminance allowing a larger range of coverage. Porous PTFE exhibits a near-perfect diffuse reflectance, resists degradation from UV light, can be molded into complex shapes, and is chemically inert, making it an attractive material for light spreading applications. The resistance of PTFE to UV light can be partly attributed to the strength of the carbon-fluorine bonds found in the material. Thickness is a critical parameter because of the mechanism of diffuse reflection. A thicker material will cause the UV to have more reflection within the porous PTFE structure before the light is able to pass completely through the material. Microporous PTFE sheet at 3 mm thickness exhibits total reflectance of over 99% in the UV and visible range, as well as close to 100% diffuse reflectance. PTFE has low UV radiation absorption properties in the 250 nm to 500 nm range. At wavelengths below 240 nm, PTFE begins to absorb UV light as carbonification begins to occur on the surface layer of the material, and chemical bonds there are severed. In conclusion, the reflectance of porous PTFE in the UV range is not only excellent but also the reflected energy is nearly perfectly Lambertian, i.e. diffuse reflectance.

A common material used in commercial UV disinfection systems are stainless steel and aluminum. While these materials are highly resistive to microbial growth, stainless steel only has 20-28% reflectance of UV light and aluminum, 80% reflectance. However, PTFE provides more than 95% reflectance of the UVC light making systems constructed of these materials more than three times effective than traditional reflectors. Aluminum is useful for applications that require spectral reflectance, but it does not produce a uniform Lambertian distribution of light like PTFE does.

An embodiment includes a UV Intensity Sensor: In order to operate the UV system efficiently and to obtain a consistently good curing result, careful monitoring of the UV output is extremely crucial. If the lamps are only replaced at set time intervals which is the conventional method, they may be replaced too soon or too late, creating needless waste of resources. The UV intensity sensor continuously monitors UV lamp intensity of a single lamp, it establishes preventive maintenance schedules for lamp systems and determines when to replace a lamp, as well as collects data for statistical process and quality control. When the UV lamps and reflectors are new, the display is set to show a 100% relative intensity. A decrease in the displayed percentage shows the gradual degradation in the UV lamp's output compared to its output when new. The user can set a low-level threshold of UV being emitted to ensure the proper dosage for an effective disinfection. According to an embodiment, a red low limit indicator light will warn the user that this threshold has been breached.

A preferred embodiment includes a detachable floor bot. Preferably the detachable floor bot comprises wireless communication and autonomous navigation capability. The wireless floor bot is configured to disinfect the floor and thoroughly disinfect shadowed areas underneath high-touch surfaces that the UV-C light from the main unit cannot reach. A study found that after routine hospital cleanings, 18% of sites under bedside tables remained contaminated with MRSA. Many other pathogens survive manual and routine cleaning from missed areas causing the transmission of viruses and bacteria to patients in the hospital setting. According to an embodiment, the low-profile floor bot is designed and configured to disinfect and maneuver underneath hospital beds, furniture, and under high-touch surface areas such as surgical tables and bedside tables, and furniture. Preferably UVC lights are emitted from all directions of the floor bot to ensure maximum disinfection. According to one embodiment, the floor bot disinfects and charges simultaneously with the main unit. According to an embodiment, a ring of LED lights surrounding the diameter of the floor bot has five different colors. The indications of each color also coordinate with the main unit: White: In motion, Yellow: Warming up, Blue: Disinfecting, Green: Complete, Red: Error/Stopped.

Innovative technology such as visual SLAM configured with Internal Measurement Unit (IMU), intelligent sensor fusion software and proximity sensors enable the robot to provide a thorough disinfection and cover the shadowed areas missed by the main unit. An embodiment comprises a proximity sensor which allows the floor bot to detect objects surrounding it. When it detects an object above it such as for example, a surgical table, or is under a hospital bed or furniture, it is configured to stop navigating and begin disinfecting. Preferably, sensor configuration enables the floor bot to avoid stuck situations and collision, and to avoid damaging furniture and walls. Smart mapping technology enables the floor bot to map, adapt and learn the floorplan as it cleans and remembers the map for future cleaning jobs. Further artificial intelligence-based algorithms comprised in the control function of the floor bot enable it to know where it's been and where it needs to go to get the job done. The floor bot is further configured to return to the main unit once its work is complete. Together, the 2 in 1 intelligent robot endeavors to drastically reduce the risk of hospital-acquired infections and provide a safer and healthier environment like none other.

Embodiments disclosed include novel technology and software and superior autonomous functionality. Embodiments disclosed include protective shields to protect lamps when not disinfecting. Embodiments disclosed can be wirelessly operated and self-controlled.

Software

Embodiments disclosed comprise Visual SLAM software and Lidar technology to map a location, create a 3D virtual map with the ability to locate itself inside the map. Embodiments are capable of building a map of an unknown environment and perform navigation, simultaneously leveraging the partially built map, using just computer vision. According to an embodiment comprising two cameras, the robot can estimate the 3D camera location and feature position more accurately. It more rapidly estimates the initial depth compared to one camera.

An embodiment includes Sensor Fusion Software, configured to merge data from multiple sensors to reduce the amount of uncertainty that may be involved in a robot navigation motion. It helps in building a more accurate world model in order for the robot to navigate, sanitize, disinfect and sterilize accurately.

An embodiment includes a UV Intensity Sensor, configured for continuous monitoring of UV intensity for maximum efficiency. According to a preferred embodiment, a proximity sensor is configured to detect the presence of nearby objects without any physical contact thereby helping avoid stuck situations, collision, and damage to furniture and walls. An embodiment includes at least one radiation sensor which receives reflected UV-C radiation, wherein said radiation sensor measures said reflected ultraviolet-C radiation, and calculates sterilization and sanitization based on predefined criteria and on reflected ultraviolet-C radiation.

According to an embodiment, the smart robot comprises a 360-degree motion sensor, and is configured to auto shut off when motion is detected. Preferably, a mobile wireless device can control the smart robot and according to an embodiment, a Smart App via any smart phone, desktop or iPad can operate the robot. One embodiment includes software configured to track the robot in real-time, obtain results, and perform analytics.

An example of a protocol for using the device is described.

Charge robot at charging station.

Program and setup robot.

Once the robot is fully charged, a notification is sent to a user wireless remote controlling device.

Authorized user to enter assigned pin on wireless device (smart phone, desktop or iPad), can check parameters of the robot (battery level, availability, track location of robot real-time, etc., and can enter a disinfection location (for example, a room number, an entire floor of a building, etc.)

The user can schedule a cleaning time or/and enable the robot to start in real time.

The robot powers on to display white LED lights.

Based on user command, the robot detaches from the charging station, and moves towards its' destination, and once it enters/reaches its' destination, the user receives a notification.

The user sends an authorization to the robot and the robot begins the operation. The LED lights change from white to yellow.

PTFE reflectors now rotate to expose UV-C lamps, which warm up for approximately 2-3 minutes. The LED lights now change from yellow to blue.

The robot begins to maneuver throughout the room even as the floor bot detaches from the main unit.

The floor bot begins to navigate independently through the room wherein both units disinfect the room simultaneously.

Once disinfection is complete, the floor bot returns to the main unit. At the point the LED light changes from blue to green.

A notification of completion is sent to the user.

The robot either proceeds to the next area in que or docks back into the charging station.

A preferred embodiment includes a smart app for recording of results, analytics, history of where and when it disinfected, history of who operated the unit at a specific time, ability to track and locate the robot real-time, check battery life of both units, and view disinfecting schedules and times.

Since various possible embodiments might be made of the above invention, and since various changes might be made in the embodiments above set forth, it is to be understood that all matter herein described or shown in the accompanying drawings is to be interpreted as illustrative and not to be considered in a limiting sense. Thus, it will be understood by those skilled in the art of systems and methods of autonomous robotic functions, especially disinfection of confined spaces, that although the preferred and alternate embodiments have been shown and described in accordance with the Patent Statutes, the invention is not limited thereto or thereby.

The figures illustrate the architecture, functionality, and operation of possible implementations of systems, methods and computer program products according to various embodiments of the present invention. It should also be noted that, in some alternative implementations, the functions noted/illustrated may occur out of the order noted in the figures. For example, two blocks shown in succession may, in fact, be executed concurrently, or the blocks may sometimes be executed in the reverse order, depending upon the functionality involved.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-accessible format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

The present invention and some of its advantages have been described in detail for some embodiments. It should be understood that although the system and process is described with reference to robotic disinfecting systems and methods the system and method is highly reconfigurable, and may be used in other contexts as well such as multi-purpose robots. It should also be understood that various changes, substitutions and alterations can be made herein without departing from the spirit and scope of the invention as defined by the appended claims. An embodiment of the invention may achieve multiple objectives, but not every embodiment falling within the scope of the attached claims will achieve every objective. Moreover, the scope of the present application is not intended to be limited to the particular embodiments of the process, machine, manufacture, composition of matter, means, methods and steps described in the specification. A person having ordinary skill in the art will readily appreciate from the disclosure of the present invention that processes, machines, manufacture, compositions of matter, means, methods, or steps, presently existing or later to be developed are equivalent to, and fall within the scope of, what is claimed. Accordingly, the appended claims are intended to include within their scope such processes, machines, manufacture, compositions of matter, means, methods, or steps.

We claim:

1. In an autonomous disinfecting system, a method comprising:

emitting UV-C light from a first unit comprising a first plurality of UV-C lamps attached to a first wireless base comprising a plurality of wheels and comprised in the housing;

releasing a second unit from a docking port comprised in the first unit, and emitting from the second unit UV-C light from a second plurality of UV-C lamps attached to a second wireless base;

shutting down the autonomous disinfecting system based on a motion detected by a 360-degree motion sensor configured to send a signal to a processing unit comprised in the autonomous disinfecting system wherein the processing unit is configured to shut down the system when it receives a signal indicating a detected movement;

independently navigating a surrounding area via a visual simultaneous localization and mapping (VSLAM) system;

communicating with a user controlled wireless device;

identifying a confined space and mapping a navigation through the identified confined space via the VSLAM coupled to a sensor, wherein the mapping further comprises estimating a length of time required to navigate through the confined space;

based on the mapping, releasing the second unit from the docking port within the first unit to disinfect spaces unreachable by the first unit in the confined space; and receiving the second unit at the docking port within the first unit.

\* \* \* \* \*